United States Patent
Rousseau et al.

(10) Patent No.: US 10,639,472 B2
(45) Date of Patent: May 5, 2020

(54) PROCESS FOR MANUFACTURING AN IMPLANT FOR FOCAL ELECTRICAL STIMULATION OF A NERVOUS STRUCTURE

(71) Applicants: Chambre de Commerce et D'Industrie de Region Paris Ile de France (ESIEE Paris), Noisy le Grand (FR); Universite Pierre Et Marie Curie (Paris 6), Paris (FR); Centre National de la Recherche Scientifique (CNRS), Paris (FR); Institut National de la Sante et de la Recherche Medicale (INSERM), Paris (FR)

(72) Inventors: Lionel Rousseau, Le Perreux-sur-Marne (FR); Gaëlle Lissorgues, Le Perreux-sur-Marne (FR); Myline Cottance, Orly (FR); Serge Picaud, Avon (FR); Julie Degardin, Ris-Orangis (FR)

(73) Assignees: Chambre de Commerce et D'Industrie de Region Paris Ile de France (ESIEE Paris) (FR); Universite Pierre Et Marie Curie (Paris 6) (FR); Centre National de la Recherche Scientifique (CNRS) (FR); Institut National de la Sante et de la Recherche Medicale (INSERM) (FR)

( * ) Notice: Subject to any disclaimer, the term of this patent is extended or adjusted under 35 U.S.C. 154(b) by 351 days.

(21) Appl. No.: 15/527,434

(22) PCT Filed: Nov. 19, 2015

(86) PCT No.: PCT/EP2015/077158
§ 371 (c)(1),
(2) Date: May 17, 2017

(87) PCT Pub. No.: WO2016/079263
PCT Pub. Date: May 26, 2016

(65) Prior Publication Data
US 2019/0083776 A1    Mar. 21, 2019

(30) Foreign Application Priority Data
Nov. 19, 2014    (FR) .................................... 14 61210

(51) Int. Cl.
*A61N 1/05*    (2006.01)
*A61N 1/02*    (2006.01)
(Continued)

(52) U.S. Cl.
CPC ........... *A61N 1/0543* (2013.01); *A61N 1/025* (2013.01); *A61N 1/05* (2013.01); *A61N 1/36* (2013.01);
(Continued)

(58) Field of Classification Search
CPC .... A61N 1/0543; A61N 1/36046; A61N 1/05; A61N 1/36; A61N 1/025; H01B 13/0036;
(Continued)

(56) References Cited

U.S. PATENT DOCUMENTS

| | | | |
|---|---|---|---|
| 2009/0118805 A1* | 5/2009 | Greenberg | ........... A61N 1/0543 607/116 |
| 2014/0121738 A1 | 5/2014 | Krafune | |

FOREIGN PATENT DOCUMENTS

| | | |
|---|---|---|
| WO | 2004073547 A2 | 9/2004 |
| WO | 2011135273 A1 | 11/2011 |
| WO | 2014126927 A1 | 8/2014 |

OTHER PUBLICATIONS

French Search Report for Application No. 1461210 dated Aug. 18, 2015.
(Continued)

*Primary Examiner* — Rex R Holmes
(74) *Attorney, Agent, or Firm* — Lerner, David, Littenberg, Krumholz & Mentlik, LLP (57) ABSTRACT

The invention relates to a process for manufacturing at least one implant for focal electrical stimulation of a nervous
(Continued)

structure, said implant being of the type including in a supporting structure a network of cavities at the bottom of which are placed microelectrodes, the cavities being bounded by walls erected and located around the microelectrodes, the supporting structure being produced beforehand by implementing the following steps: deposition and etching, in a planar manner, on an insulating substrate, of electrical contacts, of electrical tracks and of microelectrodes, first tracks electrically connecting the microelectrodes and the electrical contacts, second electrical tracks being electrically connected to a ground.

14 Claims, 6 Drawing Sheets

(51) Int. Cl.
*A61N 1/36* (2006.01)
*H01B 5/14* (2006.01)
*H01B 13/00* (2006.01)
*H05K 3/06* (2006.01)
*H05K 3/46* (2006.01)

(52) U.S. Cl.
CPC ............ *A61N 1/36046* (2013.01); *H01B 5/14* (2013.01); *H01B 13/0036* (2013.01); *H05K 3/06* (2013.01); *H05K 3/4682* (2013.01); *H05K 2201/0154* (2013.01)

(58) Field of Classification Search
CPC .... H01B 5/14; H05K 2201/0154; H05K 3/06; H05K 3/4682
See application file for complete search history.

(56) References Cited

OTHER PUBLICATIONS

International Search Report for Application No. PCT/EP2015/077158 dated Feb. 8, 2016.

\* cited by examiner

PROCESS FOR MANUFACTURING AN IMPLANT FOR FOCAL ELECTRICAL STIMULATION OF A NERVOUS STRUCTURE

CROSS REFERENCE TO RELATED APPLICATIONS

The present application is a national phase entry under 35 U.S.C. § 371 of International Application No. PCT/EP2015/077158 filed Nov. 19, 2015, published in French, which claims priority from French Patent Application No. 1461210, filed Nov. 19, 2014, all of which are incorporated herein by reference.

The present invention relates to implants for focal electrical stimulation of a nervous structure.

In particular, there is proposed a process for manufacturing an implant of this type, and a novel implant structure.

GENERAL TECHNICAL FIELD AND PRIOR ART

Implants allowing the electrical stimulation of nervous structures by means of networks of macro- or microelectrodes are currently undergoing strong development.

For example, cochlear implants are now frequently fitted to patients suffering from hearing loss further to deterioration of the hammer and anvil system; in addition, the first retinal implants are currently being tested in man for persons who have lost their sight subsequent to neurodegenerative diseases such as AMD or pigmentary retinopathy. Cortical implants have also been proposed. The progress achieved in recent years with implants for electrical stimulation of nervous structures allows the envisaging of treatment for an increasing number of motor or sensory pathologies and handicaps using these techniques.

One of the current limitations for stimulation implants is control over the focusing of stimulation signals. With regard to retinal implants for example, it has been shown that to restore almost normal vision, implants with 600 or more electrodes need to be developed. However, if focusing of stimulation currents is not properly obtained, contiguous electrodes will stimulate the same neurons without any benefit for the patient.

In patent FR 2 959 420 retinal implant structures have already been proposed comprising on a substrate:
  a network of cavities at the bottom of which are arranged stimulation microelectrodes and
  a metal grid surrounding the cavities, above the microelectrodes.

With such a structure it is possible, particularly when the grid is used as ground plane, to obtain focal stimulation of the retinal cells. At the time of stimulation by an electrode, only the neurons inside the cavity of said electrode are activated and no neuron in the other cavities is stimulated.

At the present time, these three-dimensional implants are generally fabricated by means of a 3D silicon mould with pyramids or truncated tips on which a polymer is deposited to assume the 3D shape. The electrodes and ground grid are deposited at certain points of the mould and the whole is coated with a polymer. Localised etching on this polymer creates holes for the electrodes, grid and contacts and a metal is deposited to form said electrodes, grid and contacts. A last layer of polymer is then deposited on the entire wafer. After final etching, the polymer is detached from the substrate. Release of the 3D implant is thus obtained by destroying the mould.

This fabrication technology has a certain number of limitations however.

In particular, it requires destruction of the moulds which cannot be reused and are destroyed at the end of the process to release the implants.

In addition, whilst this technology is adapted for cases having a low number of electrodes (a few tens) it proves scarcely compatible with a higher number of electrodes.

Also, it only allows flexible polymer-based implants to be produced and does not allow the fabrication of implants having rigid substrates that are thinned at the end of the process to become flexible.

Also, this manufacturing technology strongly limits the shapes that can be imparted to the cavities of the implant (these shapes being either square or round).

GENERAL PRESENTATION OF THE INVENTION

It is one general objective of the invention to propose a process for manufacturing an implant with cavities and metal or polymer network, whether or not insulated, which does not have the shortcomings of prior techniques.

In particular, it is one objective of the invention to propose a manufacturing process that is low-cost and easy to industrialise.

Another objective of the invention is to propose a manufacturing process particularly adapted for the fabrication of implants having a large number of electrodes.

A further objective of the invention is also to propose a manufacturing process adapted for the fabrication of flexible or rigid implants.

A still further objective is to provide numerous cavity geometries for an implant.

In a first aspect, the invention proposes a process to manufacture at least one implant for the focal electrical stimulation of a nervous structure, said implant on a carrier comprising a network forming cavities at the bottom of which are arranged microelectrodes, the cavities being delimited by walls erected and positioned around the microelectrodes.

Remarkably, the carrier is previously formed by implementing steps in the following order:
  planar depositing on a substrate and etching in one same basic plane: electrical contacts, electrical tracks and microelectrodes, first electrical tracks connecting the microstructures and the electrical contacts, second electrical tracks being connected to a ground,
  depositing a polymer layer on the substrate, electrical contacts, electrical tracks and microelectrodes,
  etching the polymer layer to form openings at the electrical contacts and microelectrodes,
  forming erected walls forming cavities around the microelectrodes.

The electrodes may be stimulating or receiving electrodes.

The substrate may be a rigid substrate in amorphous material e.g. of silicon glass type or the like.

The 3D implants are then detached from the substrate if the implant is a flexible implant.

These technologies can also be carried out directly on a rigid substrate that is thinned and cut to give the characteristics for implanting or using; depending on thinning, the implant will maintain greater or lesser rigidity.

Advantageously, walls forming the cavities are formed perpendicular to the surface of the implant. By "perpendicular" or "perpendicularly", here and in the entire text, is meant walls able to form angles e.g. of 85° or 95° relative to the surface of the implant.

In a first variant of a first embodiment, the substrate comprises a first polymer layer and the planar depositing and etching in one same basic plane of electrical contacts, electrical tracks and microelectrodes are performed on this first polymer layer.

In this case, the two polymer levels are etched to define the shape of the implant before erecting the walls.

In a second variant of a first embodiment, the supporting structure is previously formed by depositing an electrode on the substrate, followed by the depositing and etching of the electrical contacts and electrical tracks, and the depositing of a polymer layer after removal of the substrate subsequent to chemical etching.

In the first embodiment, a metal bonding layer is deposited and positioned at least partly on the polymer layer, electrodeposition is carried out to form metal walls surrounding the cavities, said electrodeposited walls forming at least part of a metal network surrounding the cavities.

For example, the same metal is used here between the metal walls and the metal bonding layer.

Advantageously, electrodeposition is preceded by the depositing of a mould added onto said substrate, said mould then being removed.

Advantageously, the mould and then the metal bonding layer are removed by chemical etching.

Advantageously, in one variant of the first embodiment, a metal layer is electrodeposited on said substrate, a mask is dissolved that was used to guide growth of the metal and then the metal bonding layer is dissolved to form said metal network.

Advantageously, the mould is a resin mould.

The use of said resin mould has numerous advantages.

It allows a reduction in the amount of metal used.

It also allows controlled geometric shapes to be obtained, and in particular to obtain submicron resolution.

In a second embodiment, walls in polymer are deposited to form at least part of a polymer network surrounding the cavities.

In one embodiment, the walls forming the network are connected to the electrical tracks connected to a ground.

In another embodiment, the walls forming the network are not connected to the ground-connected electrical tracks. In other words, in this case, the walls are insulating and may be in metal or polymer.

Advantageously, the walls and microelectrodes are coated with an insulating polymer layer for insulation thereof, this polymer layer then being opened e.g. by laser etching on a top part of the microelectrodes and a top part of the metal walls.

Here a process of conformal deposit type is used e.g. parylene deposition.

In this case, the ground connected to the metal electrodes lies at a different height to that of the microelectrode on the substrate.

For example, by way of illustration but not limited thereto, it is possible to deposit a density of microelectrodes/ $mm^2$ higher than a minimum density of 100 electrodes/$mm^2$.

The present invention also concerns an implant able to be obtained with the process defined above.

The present invention also concerns an implant for nervous structure focal electrical stimulation or reception, said implant comprising on a substrate: a network of cavities at the bottom of which are arranged microelectrodes, the cavities being delimited by walls erected and positioned around the microelectrodes.

It is noteworthy that the substrate, in planar fashion and in one same basic plane, comprises on a first polymer layer: electrical contacts, electrical tracks and the microelectrodes, first electrical tracks connecting the microelectrodes and electrical contacts, second electrical tracks being connected to a ground.

In addition, the substrate comprises a second polymer layer covering the electrical contacts, electrical tracks and microelectrodes, the second polymer layer being etched and having openings at the electrical contacts and microelectrodes, with walls forming cavities that lie above or project from the polymer layer.

Advantageously, the walls forming the cavities are perpendicular to the second polymer layer.

The walls forming the cavities could also have an inner flared or sloped shape.

In a first embodiment, the walls forming the cavities are metallic.

In a second embodiment, the walls forming the cavities are in polymer.

Advantageously, the implant comprises a plurality of electrical elements such as photodiodes or FET transistors integrated in the substrate and connected via electrical tracks first to a microelectrode and secondly to the metal or polymer three-dimensional structure forming the network. This is partly due to use of a planar process in one same basic plane P.

The photodiodes allow conversion of light to electricity that they transmit to the electrode.

For example, the photodiodes may be Zener photodiodes.

Advantageously, the walls forming the cavities are of general honeycomb shape.

Advantageously, the walls forming the cavities are of hexagonal shape.

Advantageously, the walls forming the cavities are circular and/or triangular and/or rectangular.

In one variant of embodiment, the walls of the cavities are separated and electrically independent of one another.

For example, the walls forming the cavities have heights of 10 µm and lower than 100 µm, and preferably between 30 and 40 µm.

For example, the walls forming the cavities have thicknesses of 2 to 50 µm, and preferably between 8 and 10 µm. For example, the density of the electrodes is associated with a pitch between each electrode which may be 70 µm for hexagonal distribution.

PRESENTATION OF THE FIGURES

Other characteristics and advantages of the invention will become further apparent from the following description that is solely illustrative and non-limiting, and is to be read in connection with the appended Figures in which.

EXAMPLES OF IMPLEMENTATION AND EMBODIMENT

General Structure of an Implant

Figure 1:
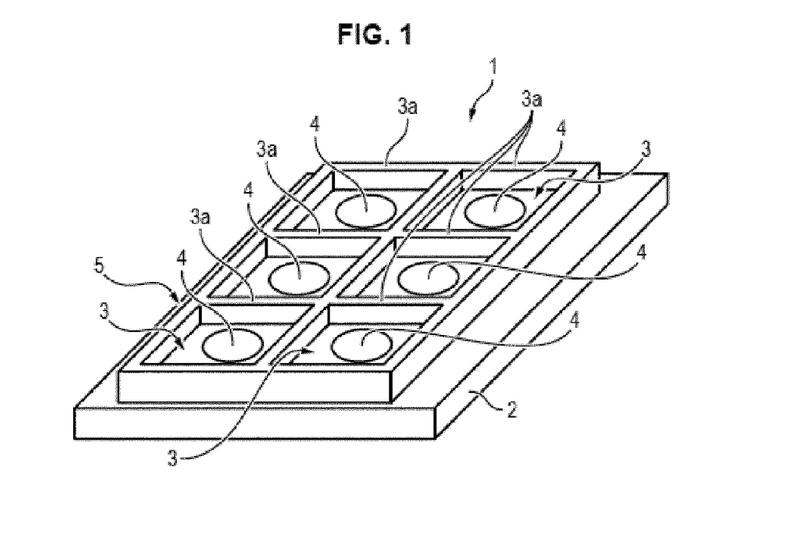
FIG. 1 is a perspective illustration of an implant with cavities which can be fabricated using one possible implementation of the proposed process.
Figure 2:
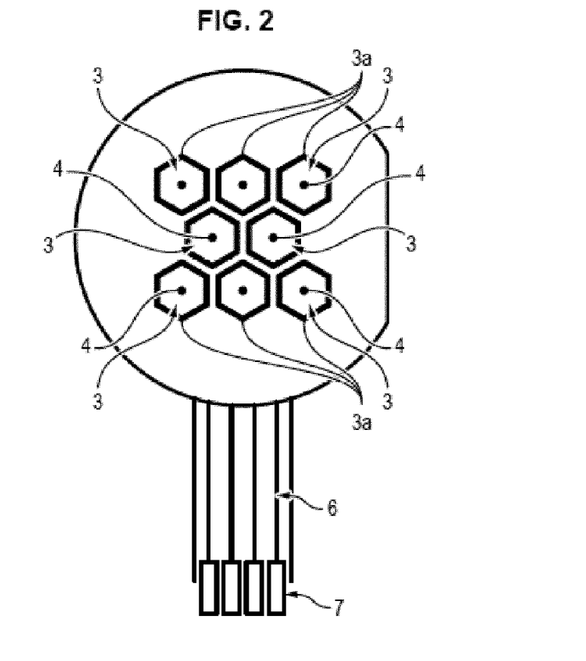
FIG. 2 is an overhead illustration of the general structure of said implant.

The implant 1 illustrated in FIGS. 1 and 2 comprises an electrically insulating substrate 2 on which a network 5 of cavities 3 is formed. Stimulation electrodes 4 are arranged at the bottom of these cavities 3.

The walls 3a defining the network 5 and cavities 3 are in metal and/or a polymer material. They extend by projecting from the plane of the electrodes 4, optionally being at least partly above the latter.

The term "network" used in the entire description means a set of interweaved walls.

The network in some embodiments may be compared to a grid of polymer walls or a rigid grid with metal walls. In other words, the walls have a certain thickness and here they are thin. The walls are of narrower thickness than the width of the cavities (or the diameter of the cavities if the cavities are round).

This network may or may not be a ground grid (i.e. a network connected to a ground).

The term wall used hereafter designates a low wall or pillar which surrounds the electrode 4 and comprises perpendicular or erected surfaces relative to the bottom of the cavities (one inner and one outer) and a top part. As a function of embodiments, bearing in mind that the inner surface surrounds the electrode 4, the outer surface may or may not also form the inner surface of another cavity and surround another electrode (cf. FIGS. 1 and 2).

These surfaces are parallel and identical in the embodiments in FIGS. 3a to 4e, and 8a and 8b, whilst the top part is perpendicular thereto. Evidently other embodiments can be envisaged. For example, the inner and outer surfaces may be angled differently.

The electrodes 4 are connected via electrical tracks 6, 6a, 6b to electrical contacts 7 for the controlling of electrical stimulations by said electrodes.

First tracks 6a electrically connect the microelectrodes 4 and electrical contacts 7.

Second electrical tracks 6b, separated from the first tracks 6a, and here deposited at the same time as the first tracks 6a on layer 10 or layer 11, are electrically connected to a ground and lie away from the microelectrodes 4.

The tracks 6, 6a, 6b, microelectrodes 4 and electrical contacts 7 lie in one same plane of the substrate, allowing a better manufacturing yield and greater implant flexibility.

Below, solely for illustrative and non-limiting purposes, geometric dimensions are given of characteristic elements of the substrate.

The electrodes typically have a thickness of less than 10 μm, and have a dimension in the plane of the substrate ranging from a few micrometres to about one hundred micrometres.

The network 5 typically has a height higher than 10 μm and lower than 100 μm. It is preferably between 30 and 40 μm.

The width or thickness of the walls 3a defined by said network 5 ranges from 2 μm for example to about fifty micrometres. Preferably, this width is between 8 and 10 μm.

The electrical tracks 6a, 6b have a width in the order of 10 μm for example and a thickness (or height) of 1 to 5 μm.

The substrate 2 has a thickness (or vertical height if the substrate 2 is horizontal) in the order of few tens of micrometres.

Example of a Process to Manufacture an Implant with Metal Electrodes

An implant structure of the type illustrated in FIGS. 1 and 2 is fabricated for example as illustrated in FIGS. 3a to 3h.

At a first step (FIG. 3a), a first electrically insulating layer, here for example a polymer layer 10, is deposited on a planar substrate 11 and for reasons of simplicity is part of this substrate. No mould is used at this stage to impart a particular three-dimensional shape to the final implant.

The layer 10 is a layer of polymer having a thickness for example of 10 to 30 μm.

This polymer may be a biocompatible polymer of polyimide type or a parylene.

This first layer could also be in a non-polymeric material such as a silicon oxide $SiO_2$.

The planar substrate 11 is in a rigid, amorphous material. It is formed for example by a Si/SiO$_2$ substrate (as illustrated in FIGS. 3a to 3h), a glass substrate or metal substrate.

At a second step (FIG. 3b) a metallised layer 12 is formed by deposition followed by planar etching of the electrical contacts 7, electrical tracks 6a, 6b and microelectrodes 4 on the polymer layer 10 (i.e. they belong to the same basic plane P that here is horizontal).

Figure 3A:
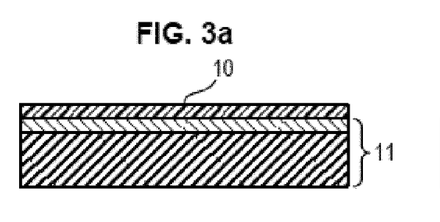
FIGS. 3a to 3h illustrate one possible embodiment of the process proposed by the invention.
Figure 3B:
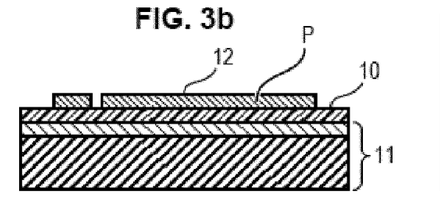

The basic plane P has a thickness containing the electrical contacts 7, electrical tracks 6a, 6b and microelectrodes 4, and is superimposed over the planar insulating substrate.

The metals used are biocompatible metals for example (gold, platinum) which can be electrodeposited.

It is also possible to modify the electrodes to reduce impedances, for example using black platinum Pt.

A non-biocompatible metal could optionally also be used but would have to be coated with a biocompatible metal with the guarantee that there would be no contact therewith over the long term.

Figure 3C:
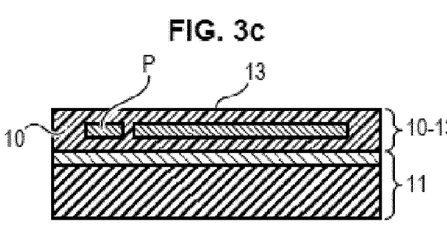

A second electrically insulating layer 13 is then deposited on the entire wafer thus formed (FIG. 3c).

This layer 13 is composed of the same polymer for example as the polymer of layer 10. Its thickness is of the same order as the thickness of layer 10.

This second layer could also be in non-polymeric material such as silicon dioxide $SiO_2$.

The metallisation of the electrical tracks 6a, 6b, electrical contacts 7 and electrodes 4 is therefore embedded in the polymer of layers 10 and 13, which then together form a planar structure.

Figure 3D:
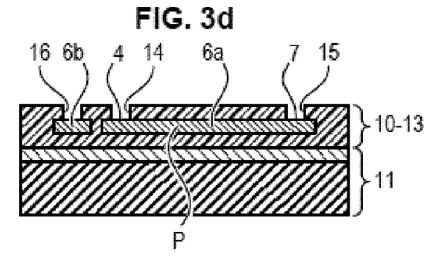

First etching in the polymer allows opening of the electrodes 4 (openings 14), of the electrical contacts 7 (openings 15) and of the electrical tracks 6a, 6b (openings 16).

The openings 16 allow connecting of the metal walls 3a with tracks 6b (FIG. 3d).

Figure 3E:
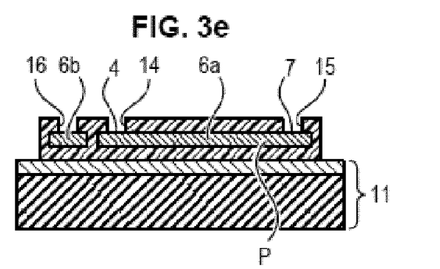

A second etching can also be provided to impart the general outer shape to the implant (FIG. 3e). This external etching step can nevertheless be implemented at a later stage.

Figure 3F:
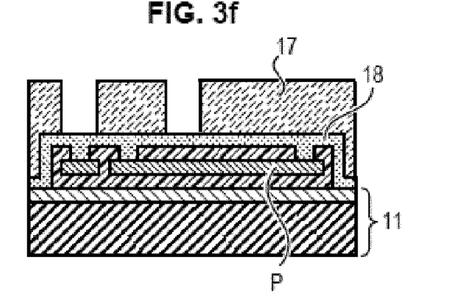

If a metal network is formed, a resin mould 17 is then deposited on the wafer obtained after step 3*d* and 3*e* (FIG. 3*f*).

This mould 17 is intended to guide the electrolytic growth of the metal which will form the ground network and define the cavity around the electrode. It defines in hollow the erected walls 3*a* of the cavities 3 which will also form the metal network 5.

It will be noted that to allow electrolytic growth, a bonding layer 18 is deposited prior to the depositing of the mould 17.

The bonding layer is advantageously in the same material as the metal of the network.

The resin of the mould 17, as a function of the polarity of the mask, is either a positive resin or negative resin. This resin must be able to be dissolved at the end of the process without degrading the two polymer layers forming the implant. The resin used is the resin marketed by Clariant for example under the trade name AZ125 NxT. Its thickness (height or vertical dimension) is typically of the order of twice the deposited thickness of the metal of layer 12 (typically 50 µm).

After electrolytic growth of the metal of the network 5 in said mould, the resin mould is dissolved (FIG. 3*g*) (chemical etching). The bonding layer 18 in the same metal as the walls 3*a* is removed by light etching after the mould 17 has been destroyed.

Figure 3G:
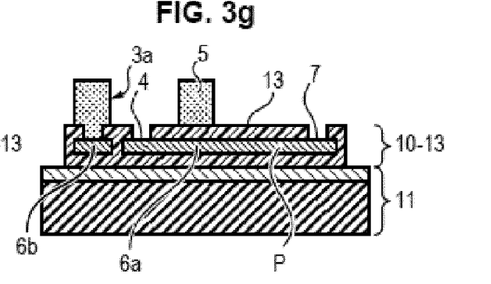

The formed implant is then detached from the planar substrate 11.

Figure 3H:
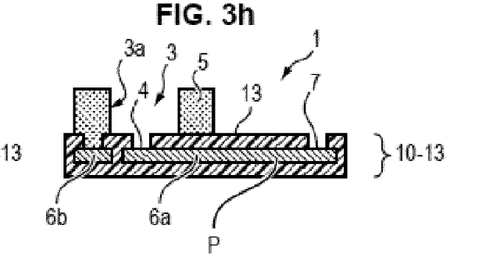

This gives the 3D implant such as illustrated in FIG. 3*h*. This implant is a flexible implant having a planar structure embedded in the polymer of layers 10 and 13 which together form the substrate 2 of the implant 1, with erected walls 3*a* above (or projecting from) the planar structure.

Example of a Process to Manufacture an Implant with Carbon Electrodes (e.g. in Diamond or Graphene)

As a variant, materials other than metals can be used for the electrodes 4.

Figure 4A:
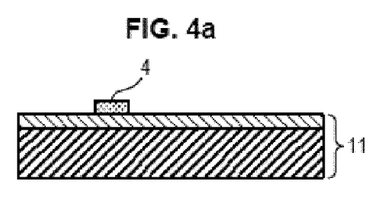
FIGS. 4a to 4i illustrate another possible embodiment of the process proposed by the invention.
Figure 4B:
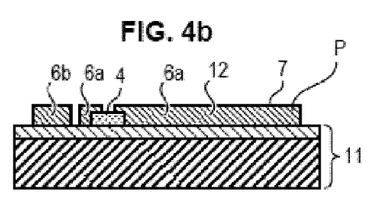
Figure 4C:
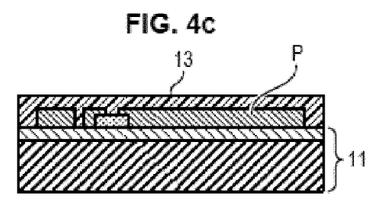
Figure 4D:
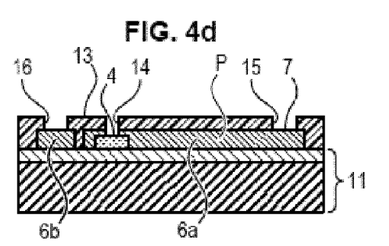
Figure 4E:
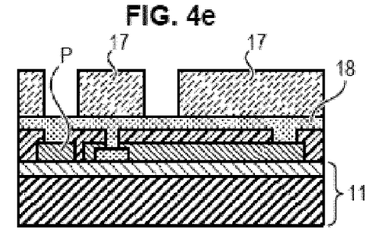
Figure 4F:
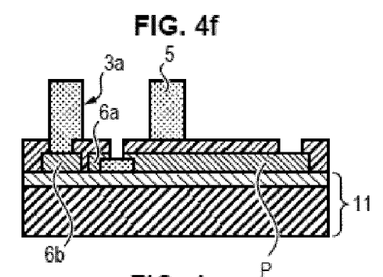
Figure 4G:
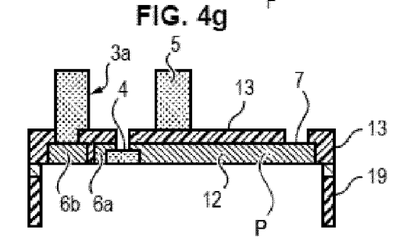
Figure 4H:
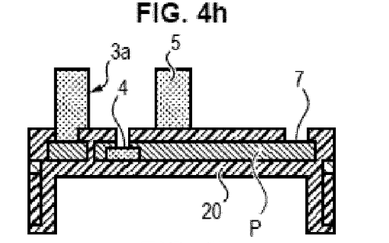
Figure 4I:
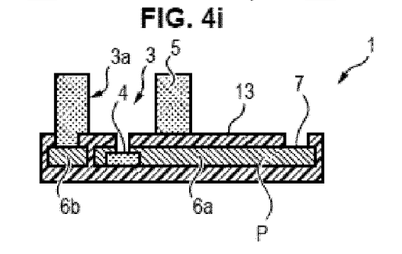

In particular, for carbon electrodes 4 (e.g. in diamond or graphene) which require high temperature deposition, the manufacturing steps may be the following:

depositing the electrodes 4 on a suitable planar substrate 11 (e.g. Si/SiO$_2$ substrate) (FIG. 4*a*);

planar depositing on substrate 11, in one same basic plane P, of a metallisation layer 12 and etching thereof to define the electrical tracks 6*a*, 6*b* (particularly those connecting the electrodes 4) and the electrical contacts 7 (FIG. 4*b*), the electrode 4 possibly being of lower height than the plane of the electrical tracks and electrical contacts 7;

depositing a polymer layer 13 on the entire wafer (FIG. 4*c*);

etching to open the electrodes 4, electrical tracks 6*a*, 6*b* and electrical contacts 7 (openings 14, 15 and 16) (FIG. 4*d*);

after depositing a bonding layer 18, depositing a resin mould 17 (FIG. 4*e*);

electrodepositing the network metal in the openings of said mould and dissolution of the resin followed by etching of the bonding layer 18 for removal thereof, the metal thus released forming the erected walls 3*a* of the cavities 3 and the reference network 5 (FIG. 4*f*);

etching the back surface of the substrate over its entire thickness to access the layers deposited on the front surface whilst leaving a rigidifying latticework 19 (FIG. 4*g*);

depositing a polymer 20 such as parylene on the back surface of the implant for insulation thereof (FIG. 4*h*) corresponding to the back surface of the basic plane P;

laser cutting the whole to impart the general desired shape to the implant (FIG. 4*i*).

This gives the 3D implant such as illustrated in FIG. 4*i*. This implant is a flexible implant having a planar structure embedded in the polymer of layers 20 and 13 which then together form the substrate 2 of the implant 1, with erected walls 3*a* above (or projecting from) the planar structure.

It will be noted that steps 4*g* and 4*h* could be omitted from the process to allow a rigid implant to be obtained instead of a flexible implant.

The implant obtained would then be a rigid implant having a substrate 2 formed by layer 11.

The example of embodiment just described concerns the case of an implant in diamond or graphene. As will nevertheless have been understood, steps 4*c* to 4*f*, even 4*g* and 4*i*, can also be implemented if metal electrodes are deposited and etched with electrical tracks and electrical contacts prior to the implementation of step 4*c*, to obtain 3D implants.

Another Possible Embodiment

Another variant of embodiment is illustrated in FIGS. 5*a* to 5*j*.

The steps illustrated in FIGS. 5*a* to 5*e* are identical to those already described for FIGS. 3*a* to 3*e*.

Figure 5A:
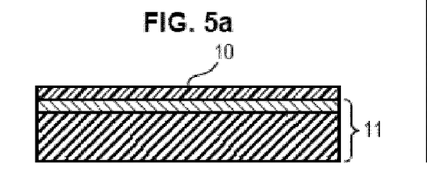
FIGS. 5a to 5j illustrate a further possible embodiment of the process proposed by the invention.
Figure 5B:
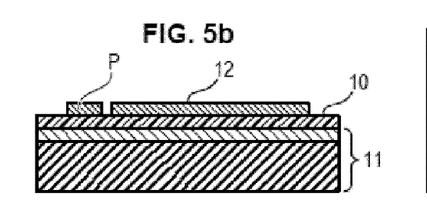
Figure 5C:
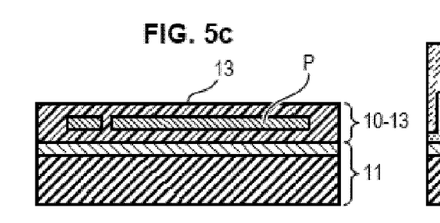
Figure 5D:
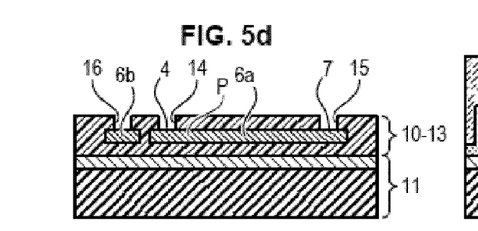
Figures 5E, 5J:
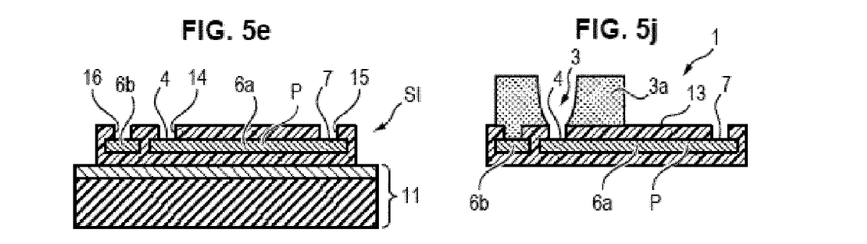
Figure 5F:
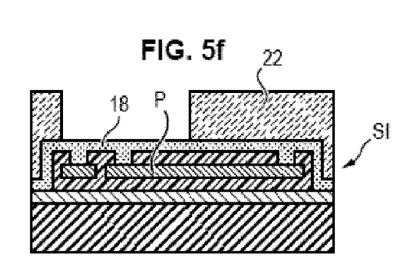

After step 5*e* therefore a carrier structure is obtained integrating in planar fashion the metallisation of the electrodes 4, electrical tracks 6*a*, 6*b* and electrical contacts 7 (integrated carrier IC) on the substrate 11 in one same basic plane P.

As a further variant, the integrate carrier IC can be independently obtained from an outside source.

Figure 5G:
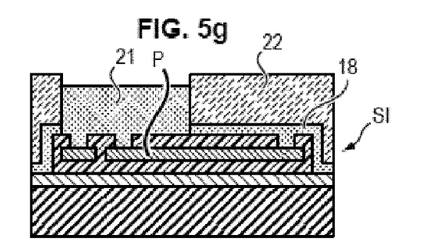
Figure 5H:
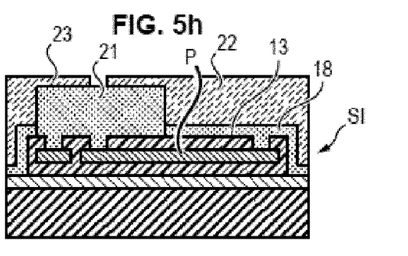

Once this carrier structure is obtained, on the area of the implant 1 intended to be covered by the network 5, a metallisation layer 21 is deposited having a thickness corresponding to the thickness of the future cavities 3 (step 5*g*).

Deposit is by electrodeposition.

A metal bonding layer 18 and a mould 22 will have been previously applied to the integrated carrier structure.

The metal bonding layer 18 may cover the entire front surface of the integrated carrier IC.

It may also be solely located on the areas of the carrier IC on which electrodeposition is performed.

Figure 5I:
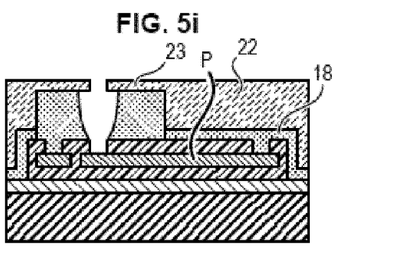

On completion of electrodeposition, complementary masking 23 of the deposited metal layer 21 is carried out (FIG. 5*h*) and said layer is etched by photolithography (FIG. 5*i*).

It will be noted here that this photolithography particularly allows flared or sloped inner cavity shapes to be obtained.

At a last step, the moulds 22, masks 23 and when applicable the carrier layer 11 are chemically or mechanically removed to obtain the implant 1 (FIG. 5*j*).

3D Geometries of the Implants and Other Variants

As will have been understood, the embodiments just described allow numerous forms to be obtained for the reference network 5, since it is possible to impart numerous 3D geometries to the hollow shapes of the different moulds 17, 22 and mask 23.

Figure 6A:
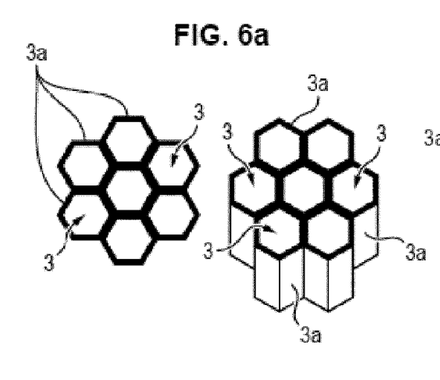
FIGS. 6a and 6b illustrate examples of cavity shapes which can be obtained by means of a process such as illustrated in FIGS. 3a to 3h, 4a to 4i and 5a to 5j.
Figure 6B:
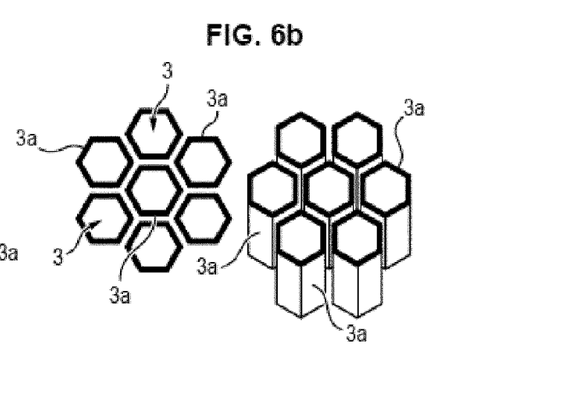

For example, as illustrated in FIGS. 6*a* and 6*b*, the cavities 3 may be honeycomb structures.

Numerous other cavity shapes are evidently possible: hexagonal, round, triangular etc., optionally with special inner 3D shapes in accordance with the inner shapes defined by the moulds and/or fabrication techniques applied.

Additionally, the proposed technology allows cavity networks to be obtained either having cavities 3 that are contiguous (then each having the same reference potential) as illustrated in FIG. 6a, or on the contrary having separated cavities 3 as illustrated in FIG. 6b (this optionally providing the possibility of acting on the reference potentials applied thereto).

Figure 7:
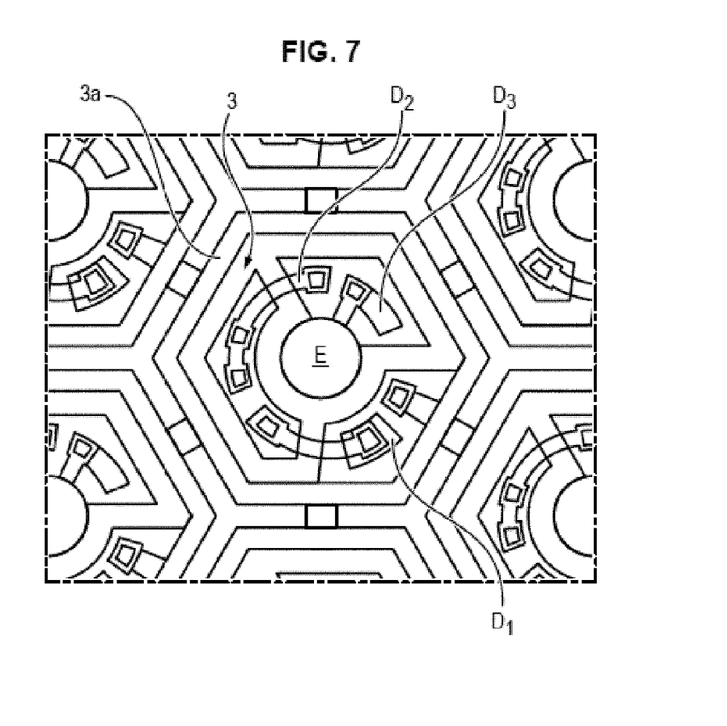
FIG. 7 is an overhead view illustrating an implant structure with photodiode on which electrodeposition can be performed using a process such as illustrated in FIGS. 3a to 3h, 4a to 4i and 5a to 5j.

As a further variant, as illustrated in FIG. 7, the structure on which electrodeposition is performed at steps 3f, 4e, 5f and following may be a semiconductor structure having a plurality of photodiodes or FET transistors D1, D2, D3 connected on one side to the electrode E of cavity 3 and on the other side to the metal surrounding the electrode E and defining said cavity 3.

Figure 8A:
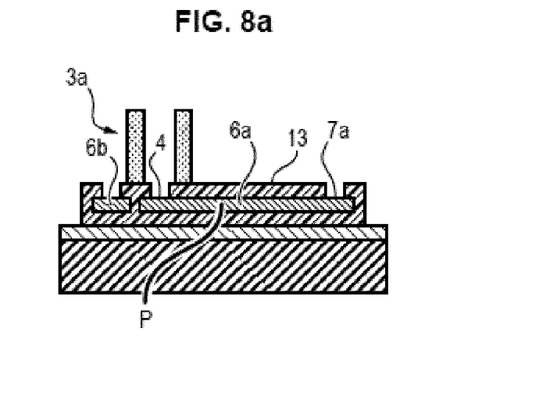
FIGS. 8a and 8b give a cross-sectional view and overhead view of an implant conforming to another possible embodiment of the invention.
Figure 8B:
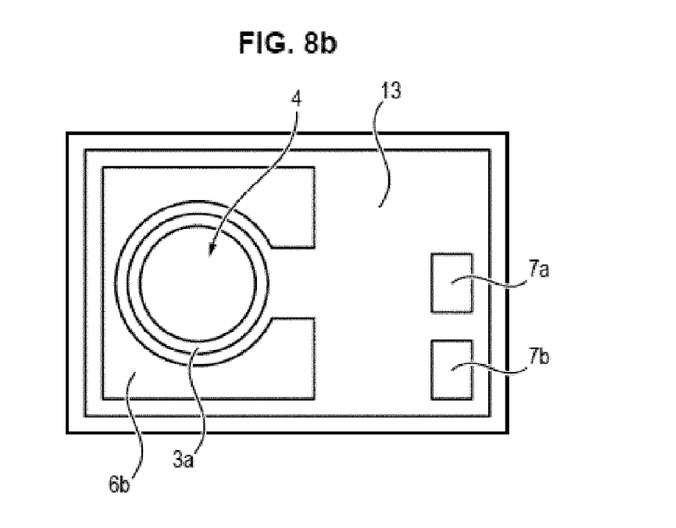

FIGS. 8a and 8b illustrate another possible embodiment wherein the walls 3a are positioned at a distance from the first tracks 6a and second tracks 6b and wherein the network 5 does not act as ground.

These walls 3a may be in polymer material, this forming the second embodiment as opposed to the first embodiment in which the walls are metallic.

However, FIGS. 8a and 8b also illustrate the case of a variant of the first embodiment in which the erected walls 3a are in metallic material (and formed by electrodeposition).

If the walls 3a are in polymer material, these walls 3a are formed by deposition of a thick, biocompatible resin of SU8 type (MicroChem). This epoxy type resin allows the forming of structures having a height of several tens of microns. Exposure to UV allows crosslinking of the exposed areas, and on development allows dissolving of the non-crosslinked areas to reveal the structure.

In FIG. 8a the ground is not in contact with the wall 3a positioned around the microelectrode 4. In this case, the walls 3a may be in metal or in polymer and act as insulating walls.

In other words, here the network is not connected to a ground and is not a ground grid.

In this electrode configuration, the electrode potential obtained (number of charges at one point) is very high (e.g. 90 mV, 125 mV and 155 mV at wall 3a heights of: 10 μm, 20 μm, 30 μm).

It was also ascertained that the greater the width of the ground plane (dimension horizontally) the lower the potential at the electrode, hence the better the electrode potential is distributed within the cavity, which allows better cell stimulation, accounted for by a greater current return with a ground plane of larger area.

It was also ascertained that the closer the ground plane lies to the electrodes the more the maximum potential at the electrode is reduced, and hence the better the electrode potential is distributed within the cavity which allows better cell stimulation. The closeness of the ground plane to the electrode seems to ensure a faster current return and hence the accumulation of charges in the medium.

It may therefore be of interest to have a fairly wide ground plane (the sizing of which must nevertheless take into account the spatial resolution of implants; for example, about ten to about forty micrometres) that is close to the electrode (for example about ten micrometres) to allow current confinement.

The cavity-shaped structure due to the height of the walls (e.g. having a height of 30 micrometres for example) also allows the generating of a more homogenous electrode potential at the electrode 4.

On the contrary, in the embodiments illustrated in FIGS. 3h, 4i, 5j the ground 6b is in contact with the wall 3a positioned around the microelectrode 4. The wall 3a in these drawings is metallic.

In other words, the network is grounded and is a ground network.

In this case, advantageously, the ground may be located on an upper surface of the wall 3a erected around the microelectrode 4, and situated above the supporting plane of the microelectrode 4, for example a polymer covering the vertical or erected surfaces of the walls 3a just above the microelectrode 4.

FIG. 8b illustrates the positioning of the ground surrounding the microelectrode 4 and allowing current return. In this case, we are in a configuration in which there is a network of cavities in which parts of a tissue come to be placed, each tissue part being insulated in the cavity from the other tissue parts in the other cavities, as in a micropipette network.

As already mentioned above, the stimulation of electrodes with a ground plane surrounding the electrode 4 and with a three-dimensional structure formed by the walls, allows more focal stimulation to be obtained. The extent of current confinement and potential at the electrode 4 is dependent on the size of the ground plane, its closeness to the electrode 4 and its positioning relative to the electrode 4. Stimulation must be sufficient (i.e. a high electrode potential at the electrodes) but also localised (by means of a ground plane) for efficient stimulation specific to a tissue region.

A planar structure in one same basic plane P for the ground surrounding the electrode and with walls erected around the electrode allows this simulation to be achieved with a high potential at the electrode 4.

As illustrated here, there are electrical contacts 7a connected via the first tracks 6a to the electrode 4, and electrical contacts 7b connected to the second tracks 6b (which are not in contact with the insulating network).

In all the FIGS. 1 to 4e and FIGS. 8a and 8b, the erected walls 3a are straight i.e. perpendicular to the substrate or to the polymer layer 13. By perpendicular, as already previously described, is meant angles of 85° to 95° for example relative to the vertical when the substrate is positioned horizontally.

This allows a greater number of electrodes per unit surface area.

Therefore, by means of the invention, better positioning of the implant is obtained on re-sealing of the tissue (subretinal implant).

Additionally, this implant provides insulation of a group of nerve cells of interest in each cavity obtained.

As a function of the electrical properties of the wall (if the wall is insulating or conducting), it is possible to vary the levels of electrical stimulation of this group of nerve cells of interest.

This novel manufacturing process has several advantages.

It is compatible with the production of 3D implants containing a very large number of electrodes.

It allows the maintaining of a planar structure in one same basic plane P throughout the fabrication of the implant. This allows an increase in manufacturing yields.

New shapes can be envisaged, for example with this technique there is no longer any limitation in the defining of cavity shapes as was the case with prior fabrication processes (square or round). It is thus possible to obtain devices of honeycomb, triangular, polygonal or other shapes. It is also possible to act on the profiles of the cavities by modifying the mould profiles.

This technology can be applied to any type of flexible or rigid implant.

The ground network is composed of metal over its entire height, which means that the entire network is conductive in the first embodiment. To obtain specific conducting areas only, it is possible to perform polymer deposition followed by localised laser opening of the active areas.

It is also possible to obtain an insulating network of erected walls deposited between the ground and the microelectrodes as described in the second embodiment, and wherein the network does not act as ground.

The 3D construction allows the implant to remain in position without the need for pinning when placed between tissues (e.g. sub-retinal implant).

The particular 3D construction associated with this manufacturing process allows a network to be produced forming cavities at the bottom of which are positioned photodiodes or FET transistors.

The invention claimed is:

1. Process for manufacturing at least one implant for focal electrical stimulation or reception of a nervous structure, said implant being of the type comprising, on a substrate, a network forming cavities at the bottom of which are arranged microelectrodes, the cavities being delimited by erected walls of the network surrounding the electrodes,
wherein the substrate is previously prepared by implementing the following steps:
planar depositing and etching on a planar insulating substrate of:
electrical contacts, first electrical tracks, second electrical tracks separated from the first electrical tracks, and microelectrodes so that the electrical contacts, first and second electrical tracks and microelectrodes belong to the same basic plane,
the first electrical tracks electrically connecting the microelectrodes and electrical contacts,
the second electrical tracks being electrically connected to a ground,
depositing an insulating layer on the planar substrate, electrical tracks and microelectrodes,
etching the insulating layer to make openings at the electrical contacts and microelectrodes,
forming a network of erected walls above the insulating layer and basic plane, and forming cavities around the microelectrodes, and
wherein a metal bonding layer is deposited at least on part of the insulating layer, electrodeposition is conducted to form metal walls surrounding the cavities, said electrodeposited walls forming at least part of a metal network surrounding the cavities.

2. The process according to claim 1, wherein a network of walls is fabricated forming a grid.

3. The process according to claim 1, wherein walls are erected to form the cavities, perpendicular to the insulating layer.

4. The process according to claim 1, wherein electrodeposition is preceded by the depositing of a mould added onto said substrate, said mould then being eliminated.

5. The process according to claim 1, wherein the planar substrate comprises a first insulating polymer layer, and the planar depositing and etching of electrical contacts, electrical tracks and microelectrodes are performed on the first insulating polymer layer.

6. The process according to claim 1, wherein the substrate is previously prepared by depositing an electrode on the planar insulating substrate followed by the depositing and etching of electrical contacts and electrical tracks-, and in that an insulating polymer layer is deposited after elimination of the substrate which follows after chemical etching.

7. The process according to claim 1, wherein the walls and microelectrodes are covered with a polymer layer for insulation thereof, this polymer layer then being opened on an upper part of the microelectrodes and on an upper part of the metal walls.

8. The process according to claim 1, wherein the metal walls are connected to the second tracks.

9. The process according to claim 1, wherein walls are deposited at a distance away from the first tracks and second tracks-.

10. Implant for the focal electrical stimulation of a nervous structure, produced according to the process defined in claim 1, said implant being of the type comprising on a substrate a network of cavities at the bottom of which are arranged microelectrodes, the cavities being delimited by erected walls, the substrate on a first planar insulating layer comprising in planar fashion:
electrical contacts, first and second electrical tracks and microelectrodes which all belong to the same basic plane superimposed over the first planar insulating layer,
the first electrical tracks connecting the microelectrodes and the electrical contacts, the second electrical tracks being connected to a ground and being separated from the first electrical tracks,
and wherein the substrate comprises:
a second insulating layer covering the electrical contacts, electrical tracks and microelectrodes, the second insulating layer being etched and having openings at the electrical contacts and microelectrodes,
a network of erected metallic walls above the second insulating layer and basic plane, forming the cavities around the microelectrodes.

11. The implant according to claim 10, wherein the network of walls forms a grid.

12. The implant according to claim 10, wherein the walls forming the cavities are perpendicular to the second insulating layer.

13. The implant according to claim 10, wherein it comprises a plurality of electrical elements integrated in the substrate and connected via electrical tracks to a microelectrode.

14. The implant according to claim 10, wherein the walls forming the cavities are in metal or polymer.

* * * * *